US009713690B2

(12) United States Patent
Somaiya et al.

(10) Patent No.: US 9,713,690 B2
(45) Date of Patent: Jul. 25, 2017

(54) METHODS AND APPARATUS FOR PRESSURE THERAPY IN THE TREATMENT OF SLEEP DISORDERED BREATHING

(75) Inventors: Chinmayee Somaiya, Turramurra (AU); Nicholas Ming Yun Yip, Kings Langley (AU); John David Oates, Castle Hill (AU); Adrian Barnes, Cammeray (AU); Christopher Kingsley Blunsden, Newport Beach (AU)

(73) Assignee: ResMed Limited (AU)

( * ) Notice: Subject to any disclaimer, the term of this patent is extended or adjusted under 35 U.S.C. 154(b) by 1579 days.

(21) Appl. No.: 12/192,247

(22) Filed: Aug. 15, 2008

(65) Prior Publication Data
US 2009/0044805 A1  Feb. 19, 2009

Related U.S. Application Data

(60) Provisional application No. 60/965,171, filed on Aug. 17, 2007, provisional application No. 61/125,066, filed on Apr. 22, 2008.

(51) Int. Cl.
*A61M 16/00* (2006.01)
*A61B 5/087* (2006.01)
(Continued)

(52) U.S. Cl.
CPC ......... *A61M 16/0066* (2013.01); *A61B 5/087* (2013.01); *A61B 5/4818* (2013.01);
(Continued)

(58) Field of Classification Search
CPC ........................... A61M 16/0066; A61M 16/69
(Continued)

(56) References Cited

U.S. PATENT DOCUMENTS

| 4,944,310 A | 7/1990 | Sullivan |
| 5,107,830 A | 4/1992 | Younes |
(Continued)

FOREIGN PATENT DOCUMENTS

| CN | 1241394 A | 1/2000 |
| CN | 1430484 A | 7/2003 |
(Continued)

OTHER PUBLICATIONS

European Search Report.
Extended European Search Report for Application No. EP13154887 dated Apr. 5, 2013.

*Primary Examiner* — Kathryn E Ditmer
(74) *Attorney, Agent, or Firm* — Lerner, David, Littenburg, Krumholz & Mentlik, LLP

(57) ABSTRACT

A controller or processor for a respiratory pressure treatment device determines an estimate of patient respiratory flow based on a measure of pressure associated with flow generated by a flow generator and a measure of frequency of the flow generator, such as a rotational velocity of a servo-controlled blower motor. The estimate can be made without data from a flow sensor. The measure of frequency may be converted to an expected pressure based on characteristics of the flow generator and subtracted from the measured pressure to determine the flow estimate. The flow estimate can be implemented in the provision of respiratory pressure treatment with the flow generator. For example, the flow estimate may be utilized to trigger expiratory pressure relief during a patient's expiration as detected with the estimated flow signal.

46 Claims, 5 Drawing Sheets

(51) Int. Cl.
*A61B 5/00* (2006.01)
*A61M 16/06* (2006.01)

(52) U.S. Cl.
CPC ....... *A61B 5/4836* (2013.01); *A61M 16/0051* (2013.01); *A61M 16/0069* (2014.02); *A61M 16/06* (2013.01); *A61M 2016/0027* (2013.01); *A61M 2205/3331* (2013.01); *A61M 2205/3365* (2013.01)

(58) Field of Classification Search
USPC ............ 128/204.18, 204.21, 204.23, 205.18
See application file for complete search history.

(56) References Cited

U.S. PATENT DOCUMENTS

| | | | |
|---|---|---|---|
| 5,390,666 A * | 2/1995 | Kimm et al. | 128/204.26 |
| 5,535,738 A * | 7/1996 | Estes et al. | 128/204.23 |
| 5,551,419 A | 9/1996 | Froehlich et al. | |
| 5,704,345 A | 1/1998 | Berthon-Jones | |
| 5,740,795 A | 4/1998 | Brydon | |
| 5,794,615 A | 8/1998 | Estes | |
| 5,927,274 A * | 7/1999 | Servidio | A61M 16/00 128/204.18 |
| 6,015,388 A | 1/2000 | Sackner et al. | |
| 6,332,463 B1 | 12/2001 | Farrugia et al. | |
| 6,336,454 B1 | 1/2002 | Farrell et al. | |
| 6,345,619 B1 * | 2/2002 | Finn | 128/204.21 |
| 6,439,229 B1 * | 8/2002 | Du et al. | 128/204.23 |
| 6,532,957 B2 | 3/2003 | Berthon-Jones | |
| 6,571,599 B1 | 6/2003 | Surjadi et al. | |
| 6,988,498 B2 | 1/2006 | Berthon-Jones et al. | |
| 7,128,069 B2 | 10/2006 | Farrugia et al. | |
| 7,152,598 B2 * | 12/2006 | Morris et al. | 128/204.23 |
| 7,225,809 B1 | 6/2007 | Bowen et al. | |
| 2003/0062045 A1 * | 4/2003 | Woodring et al. | 128/204.18 |
| 2003/0066529 A1 | 4/2003 | Truschel et al. | |
| 2004/0231670 A1 | 11/2004 | Bassin | |
| 2006/0060198 A1 | 3/2006 | Aylsworth et al. | |
| 2006/0130835 A1 | 6/2006 | Truschel et al. | |
| 2006/0196508 A1 * | 9/2006 | Chalvignac | 128/204.23 |
| 2006/0272642 A1 | 12/2006 | Chalvignac | |

FOREIGN PATENT DOCUMENTS

| | | |
|---|---|---|
| CN | 1761498 A | 4/2006 |
| CN | 1764486 A | 4/2006 |
| CN | 101014380 A | 8/2007 |
| EP | 1205203 A | 5/2002 |
| EP | 1285283 A1 | 2/2003 |
| EP | 0855923 B1 | 11/2003 |
| EP | 1393767 A | 3/2004 |
| EP | 1488743 A2 | 12/2004 |
| EP | 2289583 A2 | 3/2011 |
| JP | 2001-513387 A | 9/2001 |
| JP | 2002-505924 A | 2/2002 |
| JP | 2002-516159 A | 6/2002 |
| JP | 2003-516825 A | 5/2003 |
| JP | 2004-526470 A | 9/2004 |
| JP | 2004-529797 A | 9/2004 |
| JP | 2004-533483 A | 11/2004 |
| JP | 2006-519639 A | 8/2006 |
| JP | 2006223883 A | 8/2006 |
| JP | 05-015516 A | 8/2012 |
| WO | 9710019 | 3/1997 |
| WO | 9710868 A1 | 3/1997 |
| WO | 9812965 A1 | 4/1998 |
| WO | 01064101 A1 | 9/2001 |
| WO | 02/47747 A1 | 6/2002 |
| WO | 03/030804 A2 | 4/2003 |
| WO | 03030804 A2 | 4/2003 |
| WO | 2004/049930 A2 | 6/2004 |
| WO | WO 2004067070 A1 * | 8/2004 |
| WO | WO-2004/112680 A | 12/2004 |
| WO | WO-2005/051470 A | 6/2005 |
| WO | 2006/047826 A1 | 5/2006 |
| WO | 2006133493 A1 | 12/2006 |
| WO | 2007045036 A1 | 4/2007 |
| WO | WO 2007062400 A2 * | 5/2007 |
| WO | 2007/101297 A1 | 9/2007 |

* cited by examiner

METHODS AND APPARATUS FOR PRESSURE THERAPY IN THE TREATMENT OF SLEEP DISORDERED BREATHING

CROSS REFERENCE TO RELATED APPLICATIONS

This application claims the benefit of the filing dates of U.S. Provisional Patent Application Nos. 60/965,171 filed Aug. 17, 2007 and 61/125,066 filed Apr. 22, 2008, the disclosures of which are hereby incorporated herein by reference.

FIELD OF THE TECHNOLOGY

The present technology relates to methods and apparatus for treatment of respiratory conditions such as the conditions related to obstructive sleep apnea hypopnea syndrome (OSAHS) or obstructive sleep apnea (OSA).

BACKGROUND OF THE TECHNOLOGY

Patients with OSA have recurrent apnoeas or hypopnoeas during sleep that are only terminated by the patient arousing. These recurrent events cause sleep fragmentation and stimulation of the sympathetic nervous system. This can have severe consequences for the patient including day-time sleepiness (with the attendant possibility of motor-vehicle accidents), poor mentation, memory problems, depression and hypertension. Patients with OSA are also likely to snore loudly, thus also disturbing their partner's sleep. The best form of treatment for patients with OSA is constant positive airway pressure (CPAP) applied by a blower (compressor) via a connecting hose and mask (patient interface). The positive pressure prevents collapse of the patient's airway during inspiration, thus preventing recurrent apnoeas or hypopnoeas and their sequelae.

Positive airway pressure may be delivered in many forms. For example, a positive pressure level may be maintained across the inspiratory and expiratory levels of the patient's breathing cycle at an approximately constant level. Alternatively, pressure levels may be adjusted to change synchronously with the patient's breathing cycle. For example, pressure may be set at one level during inspiration and another lower level during expiration for patient comfort. Such a pressure treatment system may be referred to as bi-level. Alternatively, the pressure levels may be continuously adjusted to smoothly replicate changes in the patient's breathing cycle. A lower pressure setting during expiration may generally be referred to as expiratory pressure relief.

In providing such changes to pressure and/or detecting conditions for making adjustments to the treatment pressure, it can be helpful to have a measure of patient respiratory flow. For example, a measure of patient respiratory flow may be utilized to detect when a patient changes from inspiration to expiration for determining when to deliver expiratory pressure treatment settings or inspiratory pressure treatment settings. Similarly, a measured patient respiratory flow signal may be utilized to detect patient flow limitation for purposes of making treatment pressure adjustments. Such adjustments are illustrated in the patent in U.S. Pat. No. 5,704,345. For these purposes, a measured flow signal may be derived from a flow sensor such as a differential pressure transducer or pnuemotachograph.

It may be desirable to develop further methods and devices for estimating flow to improve existing methods and devices and/or to develop new pressure treatment and detection methods and devices.

SUMMARY OF THE TECHNOLOGY

Aspects of the present technology involve methods for a respiratory flow generating apparatus. In one method, a measure of pressure produced by a respiratory flow generating apparatus and a measure of a frequency of the respiratory flow generating apparatus are determined. The method then derives an estimate of patient respiratory flow as a function of the measure of pressure and the measure of frequency. In some embodiments, the measure of frequency may be a rotational velocity. Moreover, the deriving of the estimate may further include determining an expected pressure as a function of the measure of frequency and may further include calculating a difference between the determined expected pressure and the measure of pressure. Pressure treatment by the respiratory flow generating apparatus may be set or adjusted as a function of the derived estimate of respiratory flow.

In one embodiment, the technology encompasses an apparatus for generating respiratory flow. The apparatus may optionally include a patient interface to carry a flow of breathable gas to a patient. The apparatus may further include a flow generator coupled with the patient interface to generate a flow of the breathable gas through the patient interface. The apparatus may also include measurement sensors such as a pressure transducer to provide a pressure signal indicative of pressure in a portion of the patient interface or associated with the flow generator and a tachometer to provide a velocity signal indicative of a speed of the flow generator. The apparatus may also be provided with a controller to control the flow generator. The controller is coupled with the pressure transducer to process the pressure signal and it is coupled with the tachometer to process the velocity signal. The controller may be configured and adapted to control a method for estimating patient respiratory flow or to set delivered treatment pressure by a method as described herein such as by determining a measure of pressure with the pressure signal, determining a measure of frequency with the velocity signal and deriving an estimate of patient respiratory flow as a function of the measure of pressure and the measure of frequency.

In a further embodiment, a system for delivering respiratory flow to a patient includes an interface means to carry a flow of breathable gas. The system may also include a flow means, coupled with the interface means, for generating the breathable gas. The system may have a pressure sensing means for measuring pressure and for generating a pressure signal representing the measured pressure of the breathable gas as well as a frequency sensing means for measuring a frequency of the flow means and for generating a frequency signal representing the measured frequency. The system will typically also include a processing means for processing the pressure signal and the frequency signal. The processing means may be configured or adapted for processing a determination of a measure of pressure with the pressure signal, a determination of a measure of frequency with the frequency signal and a derivation of an estimate of patient respiratory flow as a function of the measure of pressure and the measure of frequency. The processing means may also be configured for controlling a generation of pressure with the flow means as a function of the derived estimate of respiratory flow. In an embodiment of the system, changes to pressure treatment may be delivered in synchrony with a patient's respiratory cycle without a flow sensor or utilizing a signal from a flow sensor.

In another embodiment, methodology of the technology may be encoded on an information-bearing medium as software or firmware. For example, an information-bearing medium may include processor-readable information or processor control instructions. The processor-readable information may control an apparatus for providing pressure treatment therapy. The processor-readable information or processor control instructions may include steps that implement determining a measure of pressure produced by a flow generator, determining a measure of frequency of the flow generator and deriving an estimate of patient respiratory flow as a function of the measure of pressure and the measure of frequency.

Further embodiments and features of the technology will be apparent from the following detailed disclosure, claims and drawings.

BRIEF DESCRIPTION OF DRAWINGS

The present technology is illustrated by way of example, and not by way of limitation, in the figures of the accompanying drawings, in which like reference numerals refer to similar elements including.

DETAILED DESCRIPTION

Figure 1:
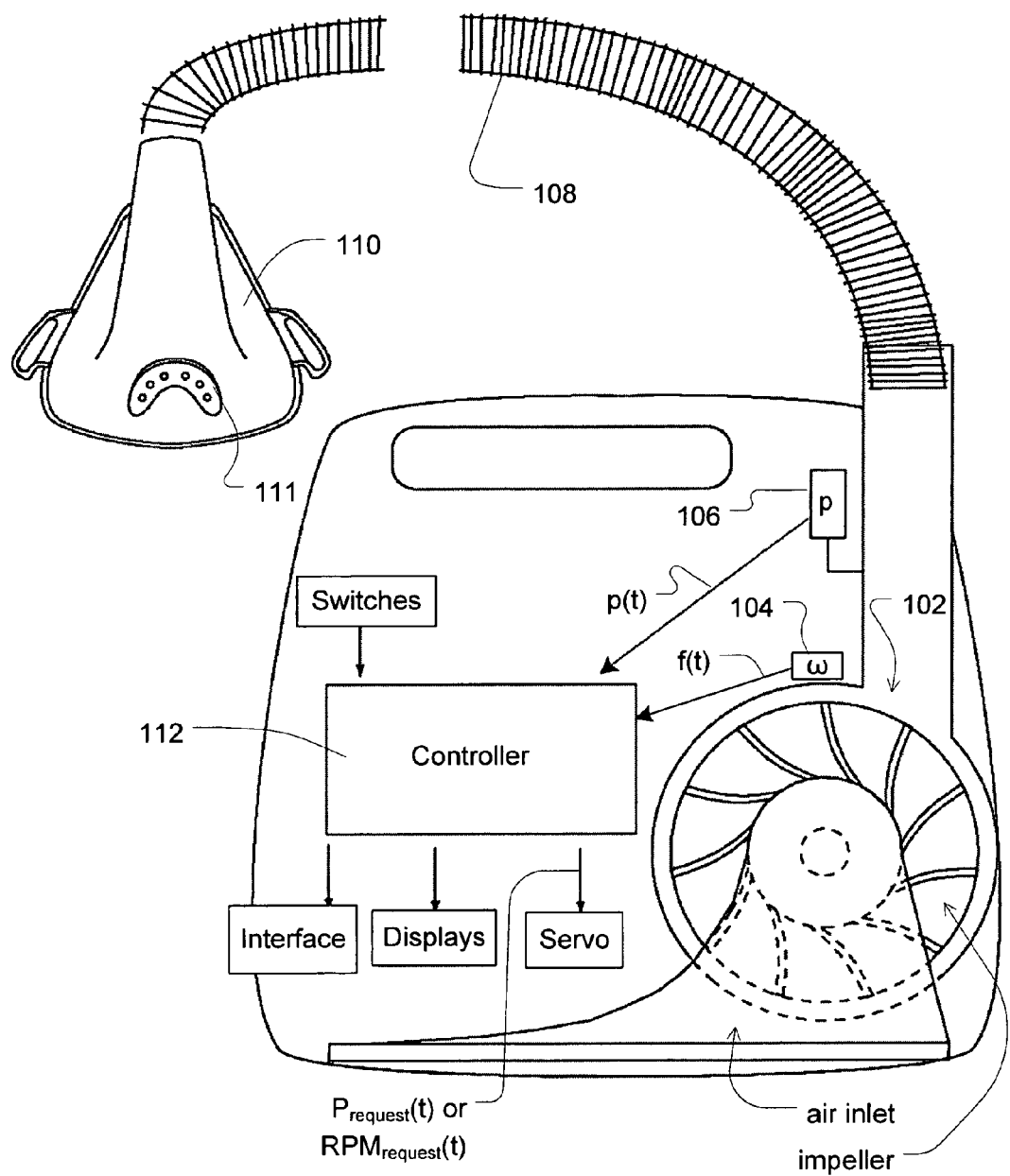
FIG. 1 shows example components of an apparatus for respiratory flow estimation and pressure treatment based thereon.
Figure 2:
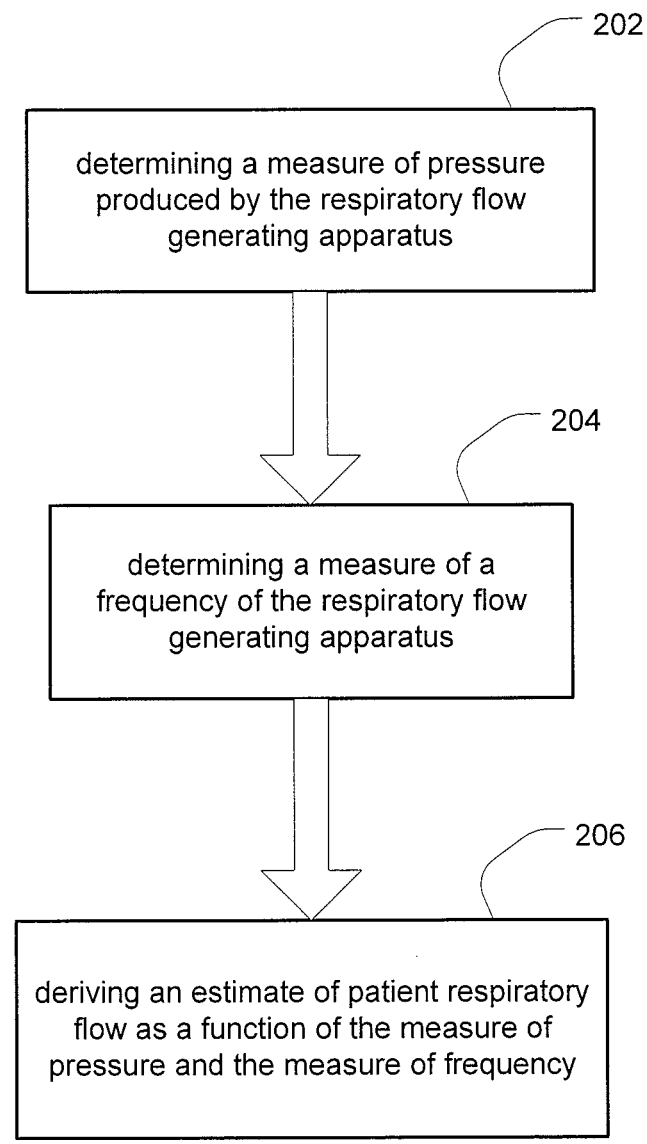
FIG. 2 is a flow chart for a method for a pressure treatment or flow estimation apparatus of the present technology.

In reference to FIG. 1, the present technology may be implemented with a pressure treatment delivery device that may include a flow generator such as a servo-controlled blower 102. The blower 102 will typically include an air inlet and impeller driven by a motor (not shown).

In the embodiment illustrated in FIG. 1, a frequency sensor 104 is provided. The sensor may be configured to measure the rotational velocity of the blower. For example, a tachometer may measure the revolutions per minute (RPM) of the blower's motor or the blower's impeller. The frequency sensor 104 may be configured to generate a frequency signal f(t) indicative of the measurements of the sensor.

The device of FIG. 1 may further include a pressure sensor 106, such as a pressure transducer. The pressure sensor 106 is configured to measure the pressure generated by the blower 102. In this embodiment, the pressure sensor 106 is proximate to the blower 102 but may be located downstream of the blower as desired. The pressure sensor 106 generates a pressure signal p(t) indicative of the measurements of pressure. The pressure sensor 106 and frequency sensor 104 have only been shown symbolically in FIG. 1 since it is understood that other configurations and other components may be implemented to measure the frequency and pressure associated with the blower 102.

The pressure treatment delivery device will also typically include a patient interface such as an air delivery conduit 108 and a mask 110 to carry a flow of air or breathable gas to and/or from a patient. The blower 102 can be coupled with the air delivery conduit 108 and the mask 110 so as to provide the breathable gas from the blower 102. Exhaust gas can be vented from the patient interface via an exhaust 111.

The frequency f(t) and pressure p(t) signals may be sent to a controller or processor 112. Optional analog-to-digital (A/D) converters/samplers (not shown separately) may be utilized in the event that supplied signals from the frequency and pressure sensors are not in digital form and the controller is a digital controller. Based on input signals from these sensors and/or other optional sensors, the controller may in turn generate blower control signals. For example, the controller may generate an RPM request signal to control the speed of the blower 102 by setting a desired frequency or rotational velocity set point and comparing it with the measured condition of the frequency sensor. Alternatively, such changes may be based on determining a desired pressure set point and comparing it with the measured condition of the pressure sensor. Typically, such changes to the motor speed are accomplished by increasing or decreasing supplied motor current with the servo based on determined differences between set and measured conditions such as in a closed loop feedback fashion and translating the difference to current. Thus, the processor 112 or controller may make controlled changes to the pressure delivered to the patient interface by the blower 102. Optionally, such changes to pressure may be implemented by controlling the exhaust with a mechanical release valve (not shown) to increase or decrease the exhaust while maintaining a relatively constant blower speed.

The controller or processor 112 is typically configured and adapted to implement particular control methodology such as the methods described in more detail herein. Thus, the controller may include integrated chips, a memory and/or other control instruction, data or information storage medium. For example, programmed instructions encompassing such a control methodology may be coded on integrated chips in the memory of the device or such instructions may be loaded as software or firmware using an appropriate medium. With such a controller or processor, the apparatus can be used for many different pressure treatment therapies, such as the pressure treatments previously mentioned, by adjusting a pressure delivery equation that is used to set the speed or pressure of the blower or the exhaust venting by the release valve.

For example, based on such a configuration, an embodiment of the system may determine or estimate a patient respiratory flow, even without a flow signal from a flow sensor, and then adjust the pressure treatment delivered by the device based on patient respiratory conditions detected from or with the estimated flow signal. While the flow characteristics of the hose to the mask may also impact pressure determinations, such a flow estimation model can be based on the premise that in an rpm-controlled system the load perturbations (i.e., patient respiratory flow) are reflected in the pressure output of the device. Similarly, in a pressure-controlled system the load perturbations will be reflected in the rpm output of the device.

Thus, in one embodiment, two measures, such as pressure and flow generator system frequency (e.g., a rotational velocity of the blower such as RPM) taken together can give a measure of flow. In one suitable patient flow estimate, the measured pressure and an expected pressure value derived from the frequency measure may both be utilized to derive the flow as a function thereof. This can be illustrated with the following function:

$$\text{Flow} = \text{function}(P_M - P_{RPM\_derived})$$

Where:

$P_M$ is a measured pressure;

$P_{RPM\_derived}$ is an expected pressure at a particular flow that is determined or calculated from a measured system variable other than pressure such as frequency or rotational velocity (e.g., RPM) of the blower. Depending on the flow generator characteristics and required accuracy, it can also be either a fixed value or calibrated value.

In one embodiment, $P_{RPM\text{-}derived}$ may be determined or calculated by a static fan curve as follows:

$$P_{RPM\text{-}derived} = K_2 * \omega^2 + K_1 * \omega + K_0$$

Where:

$\omega$ is an angular frequency of the flow generator (which may also be referred to as angular speed, radial frequency, and radian frequency); and $K_2$, $K_1$ and $K_0$ may be experimentally pre-determined constants for relating an experimental measure of delivered pressure to a blower's measured angular frequency based on the particular structural characteristics of the flow generator or blower (e.g., impeller design). Optionally, in the case of small constants, the constants may be uniformly scaled up to reduce operational overhead of decimal point operations on a device's processor or controller.

In one embodiment, the flow may then be determined as a function of the difference between $P_M$ and $P_{RPM\_derived}$ by utilizing the following equation:

$$\text{Flow} = A_3 * x^3 + A_2 * x^2 + A_1 * x + A_0$$

Where:

x is $P_M$ minus $P_{RPM\_derived}$ as previously described; and $A_3$, $A_2$, $A_1$ and $A_0$ may be experimentally pre-determined constants for relating an experimental measure of flow to a function of the blower's measured angular frequency and measured pressure based on the particular structural characteristics of the system.

However, given the limitations of 32-bit processing, it was found that the computational complexity was quite high for arriving at the desired level of performance of flow linearization using the above equation. Thus, in another embodiment of the technology, in order to simplify the determination, a look up table may be pre-formed based on the above equations. A suitable table may be pre-calculated based on a range of input measures of frequency and a range of input measures of pressure using the formulas. The output of the table would then be a derived instantaneous flow value based on an input instantaneous measure of pressure and an input instantaneous measure of frequency as previously described.

In a still further embodiment of the technology, the derived flow values may be determined from the difference between the measured pressure and the frequency derived pressure (e.g., $P_M - P_{RPM\_derived}$). Thus, the flow may be more simply estimated by the following equation:

$$\text{Flow} = P_M - P_{RPM\_derived}$$

Where:

$P_M$ is a measured pressure; and $P_{RPM\_derived}$ is an expected pressure that is determined or calculated from a measured system variable other than pressure such as frequency or rotational velocity (e.g., RPM or $\omega$ of the blower by any method previously discussed.

Although this particular estimate is not linearized, it can give an estimate of flow excursion. Therefore, it is quite suitable for algorithms that are dependent on cycle detection. In the absence of further processing, it may not alone be highly suitable for algorithms that require more accurate flow value or more accurate flow shape. However, its simplicity can make it particularly suitable for implementation either as a hardware component to reduce a system processor load or as firmware/software for a system processor.

In a system that employs a continuous system exhaust flow or leak with which the patient respiratory flow is combined, the above determined flow values may be further processed to separate the system or leak flow from the patient respiratory flow by a suitable operation such as one illustrated by the following equation:

$$\text{Respiratory Flow} = FLW - LPF(FLW)$$

Where:

FLW is continuously or periodically determined flow values derived from any of the previously described methods; and LPF(FLW) is a low pass filtering operation on the flow values with the filtering operation being chosen to remove a constant component of the flow that can be associated with a relatively constant leak or system flow. An example operation may be low pass filtering with a time constant of 10 seconds.

Figure 3:
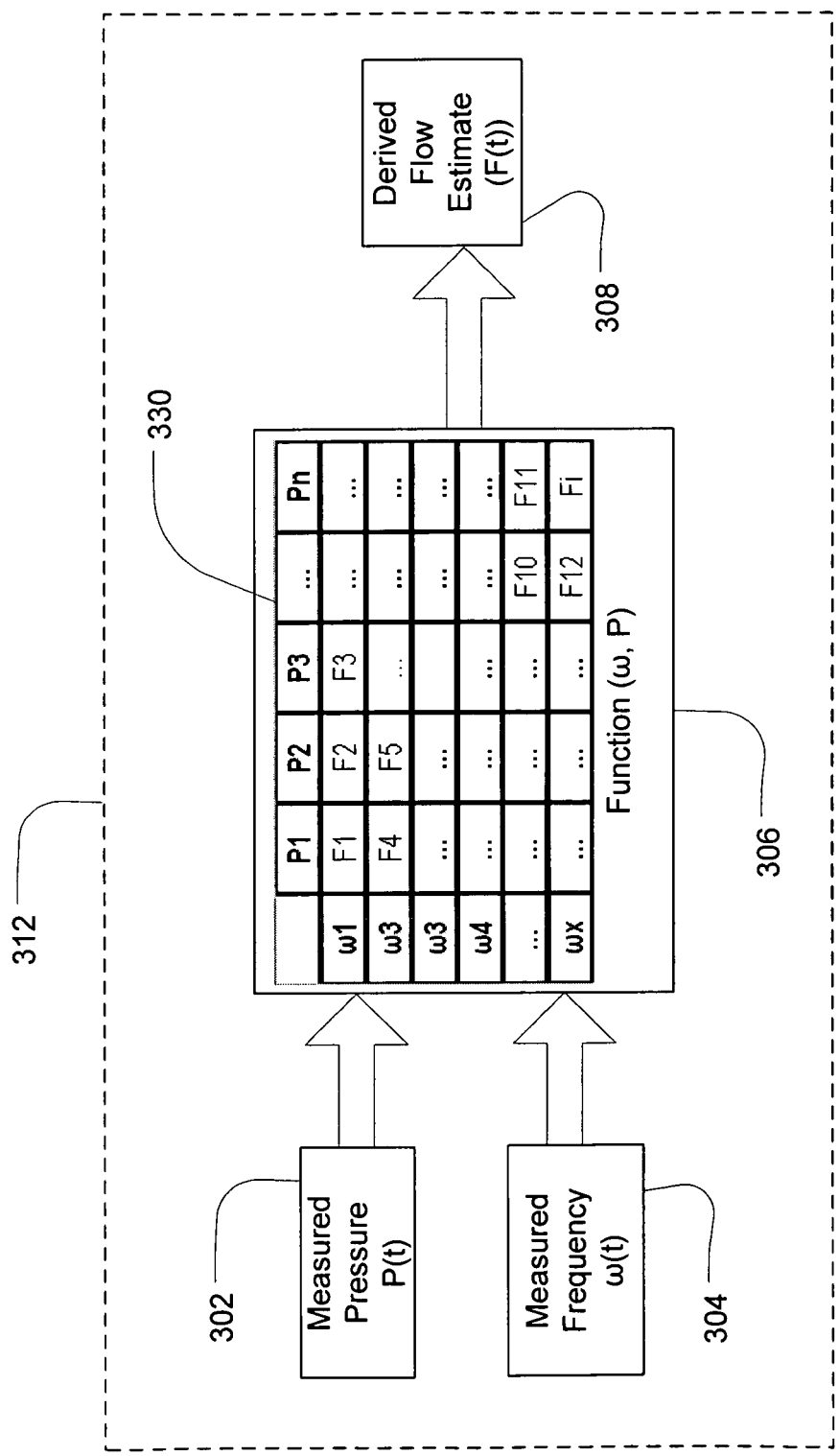
FIG. 3 is an illustrative input/output diagram for a control circuit or processor implementing flow estimation technology.

FIG. 3 illustrates the flow estimate methodology with respect to a controller or processor 312. A measured pressure value signal 302 (p(t)) and a measured frequency value signal 304 ($\omega$(t)) are input to a flow estimate algorithm 306 for deriving an estimated flow value signal 308. The flow estimate algorithm 306 is based on any of the calculations or functions as previously discussed such as one or more flow lookup tables 330.

An estimate of flow (e.g., estimated patient respiratory flow) made by any of the methods discussed herein may then be used in any suitable flow-based determinations typically made by a pressure treatment device. For example, the derived flow estimate can be used to make a change in pressure upon detection of features of the patient respiratory cycle. In an illustrative embodiment, the derived flow estimate may be used to trigger an expiratory pressure relief. In such an embodiment, a ratiometric trigger threshold, such as a trigger threshold that is a function of the peak respiratory flow, may be utilized to detect the onset of expiration. Utilizing such a trigger in particular combination with any of the above estimates of flow that might deviate marginally from actual patient flow provides for a more reliable or resilient respiratory cycle detection and appropriate pressure response.

In this embodiment, the technology can be implemented according to the following pseudo code:

```
if (RespiratoryFlow   >   PeakRespiratoryFlow/Y)   or
   (EPR has been on for over 15 sec) then
      Turn EPR off
else if (RespiratoryFlow < 0) then
      Turn EPR on
```

Where:

RespiratoryFlow is a derived flow estimate made by any of the methods previously described;

PeakRespiratoryFlow is a pre-peak respiratory flow value, such as a peak determined in a prior respiratory cycle;

Y is some divisor of the peak respiratory flow (e.g., 4); and

EPR is a procedure that implements a reduction in the delivered treatment pressure setting for patient comfort.

In this embodiment, a bi-level pressure treatment therapy may be generated such that a reduced pressure level is delivered by the EPR during patient expiration and a higher treatment pressure level without the EPR reduction is delivered during patient inspiration. Depending on the flow generator characteristics or settings, such as a motor fall time and rise time, the changes between an inspiratory level and an expiratory level may be gradual such that a smoother pressure change between the inspiratory pressure treatment levels and the expiratory pressure treatments may be effected.

Figure 4:
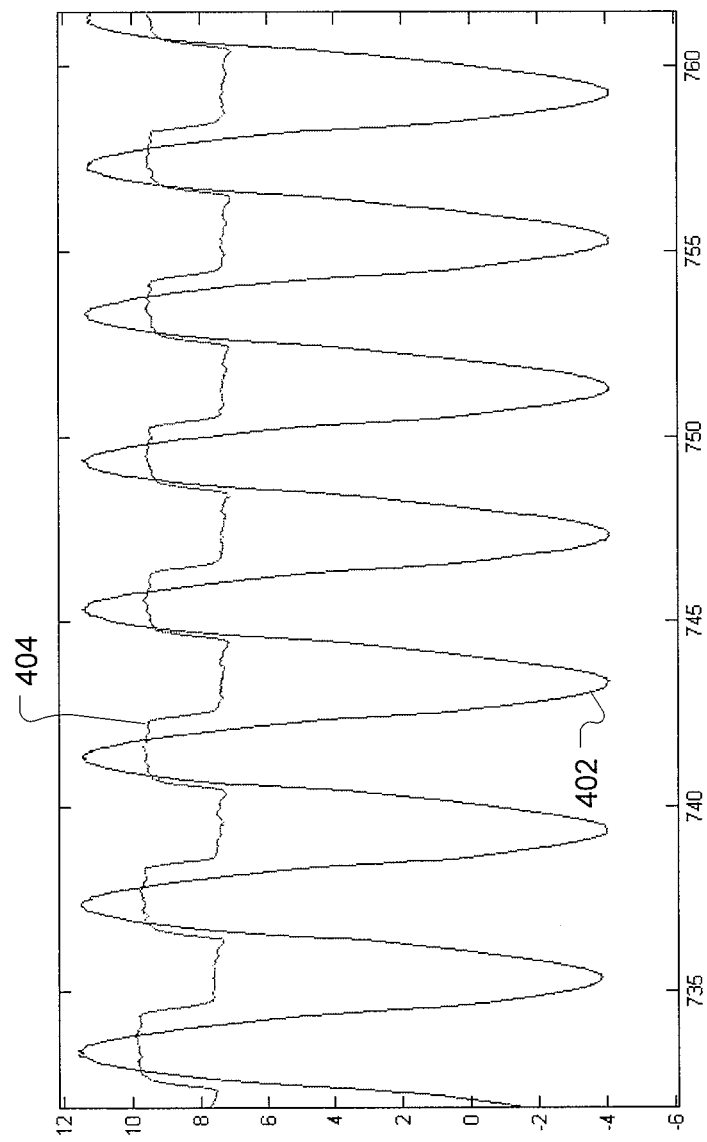
FIG. 4 is a graph of an exemplary pressure treatment waveform implemented by a pressure treatment apparatus utilizing the present flow estimation technology.

An example pressure waveform that may be delivered in accordance with the present technology is illustrated in the graph of FIG. 4. FIG. 4 includes a plot of a patient simulation flow waveform 402 that has been generated by a patient flow simulation apparatus. The patient flow simulation apparatus was coupled with the patient interface of a pressure treatment device that implements flow estimation technology described herein. FIG. 4 also includes a graph of a pressure waveform 404 generated using the flow estimation and triggering technology discussed herein within the pressure treatment device. The graph illustrates that the device may deliver pressure adjustment in synchrony with the cycle of the patient simulation flow waveform 402 based on the estimated flow methodology.

A pressure treatment device can be affected by changes to pressure in the system introduced by the patient's respiratory cycle. In the event that the sensors utilized for control of pressure levels to the mask of the patient interface are located proximate to the flow generator, rather than the mask of the patient interface, undesirable swings in mask pressure can be induced by the patient's respiration. These undesirable mask pressure swings can be adjusted with the controller to maintain more steady pressure levels by utilizing the present estimated patient flow technology.

For example, in another embodiment, the pressure treatment device controls pressure rather than controlling motor rpm and a pressure sensor used for the control is located at or proximate to the flow generator. In the embodiment, the measure of pressure that will be used in the feedback loop for pressure control is adjusted as a function of the estimate of flow. This adjustment is implemented in a predictive manner in an effort to impede mask swings induced by the patient's respiratory cycle. For example, the measured control pressure may be adjusted according to the following method:

$$\text{MeasuredPressure}_{adjusted} = \text{MeasuredPressure} - \text{FlowFactor}$$

Where:

FlowFactor is a function of an estimate of flow determined by any of the previously described methods.

In one embodiment, this function of the estimate of flow may be multiplying the estimate by a value K, where K is a value that is different for positive flow (e.g., patient inspiration) and than for negative flow (e.g., patient expiration). The value for K may be experimentally chosen for positive and negative flow as desired to identify optimum values for swing reduction that generate more steady mask pressure in response to patient respiration.

The adjusted measure of pressure may then be applied to a pressure control feedback loop such as a control loop implementing Pseudo Derivative Feedback (PDF) control as follows:

$$\text{Error} = \text{DesiredPressure} - \text{MeasuredPressure}_{adjusted}$$

$$\text{MotorCommand} = P * \text{Error} + I \int \text{Error}$$

Where:

DesiredPressure is a determined treatment pressure setting such as an inspiratory or expiratory treatment pressure level;

MeasuredPressure$_{adjusted}$ is the adjusted pressure as previously described;

P and I are factors chosen for translation of the pressure setting to an adjustment of the current applied to the motor of the flow generator for adjusting a particular motor's speed based on the characteristics of the motor.

Figure 5:
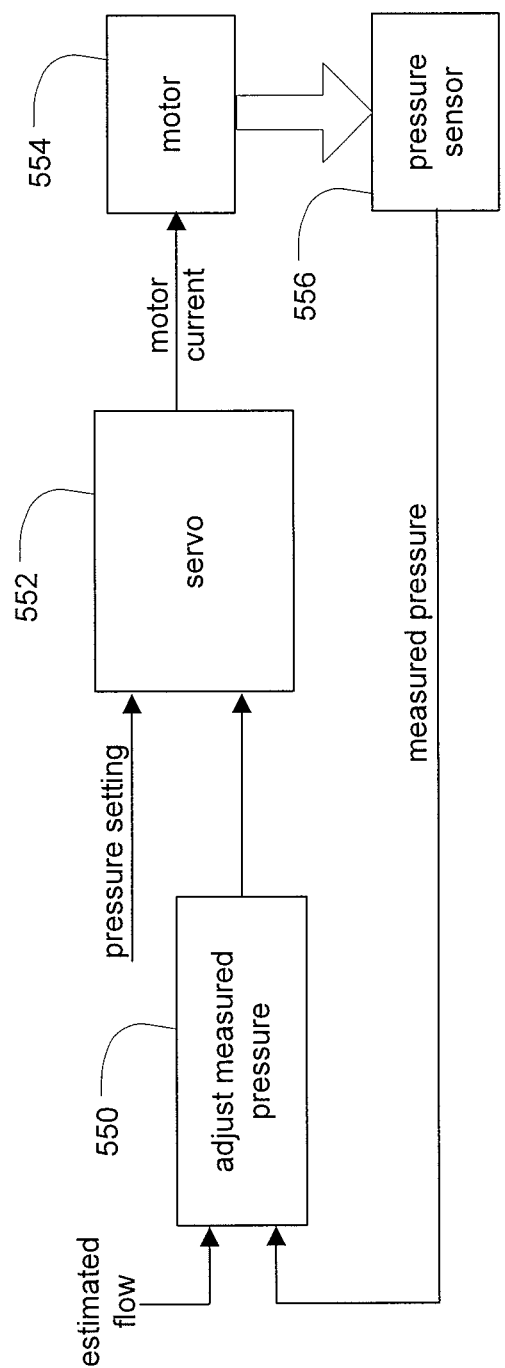
FIG. 5 is a diagram illustrating suitable components of a feedback control loop of a pressure treatment device utilizing flow estimation technology for mask swing adjustment.

Controller components of such swing compensation control are illustrated in FIG. 5. An estimated flow value or signal is supplied to a measured pressure adjustor 550 along with a pressure value or signal measured by a pressure sensor 556. A pressure setting value or signal is supplied to the servo 552 along with an adjusted measured pressure value or signal. Based on these signals, the servo adjusts the motor current for controlling the output or speed of the motor 554 of the flow generator to thereby adjust the pressure delivered by the flow generator device to predictively reduce mask pressure swings induced by patient respiration.

In a still further embodiment, swing compensation control may be implemented with a modified version of the swing control equation. In such an embodiment, the pressure at the flow generator is controlled by comparing a desired pressure set point with the measurement from the pressure sensor. In other words, the flow generator may be controlled so that a pressure set point is equal to a measure of pressure determined from a pressure sensor at the flow generator.

However, because the pressure at the flow generator is controlled to the set point, the pressure fluctuations at the mask are a result of the flow related pressure drop through the patient interface or delivery circuit. This may be represented by the following equation:

$$\text{MaskPres} = \text{PresSetPoint} - \text{PresLossInDeliveryCircuit}$$

Where:

MaskPres is the pressure in the patient mask or patient interface,

PresSetPoint is a desired pressure or target pressure,

PresLossInDeliveryCircuit is a pressure loss due to the impedance of the delivery circuit.

Pressure fluctuations in the mask can be reduced by modifying the measured pressure as previously described as follows:

$$\text{MeasuredPressure}_{adjusted} = P_M - \text{FlowFactor}$$

where $P_M$ is a measure of pressure from a sensor such as a pressure transducer.

The FlowFactor may represent the pressure drop in the delivery circuit and can be assumed to be proportional to an estimate of flow. For example, $$\text{FlowFactor} = \text{ImpedOfDeliveryCir} * \text{Flow}$$

where

ImpedofDeliveryCir is the impedance of the delivery circuit or patient interface, Flow is an estimate of flow as previously determined.

However, since the estimate of flow may be considered to be a function of the pressure drop across the flow generator as previously described, then the pressure drop can be approximated to be proportional to the estimate of flow according to the following equation:

Flow=PresDropAcrossTurbine/ImpedanceofTurbine;

where

PresDropAcrossTurbine is a pressure drop across the flow generator such as one determined as a difference between a measured pressure and a derived pressure as previously described (e.g., $P_M - P_{RPM\_derived}$), and ImpedanceofTurbine is an impedance of the flow generator which may depend on the particular design of the flow generator and may be predetermined and/or preset into the memory of the controller of the system.

By combining the preceding flow factor equation with this immediately preceding flow equation, an explicit computation of one of the previously described estimates of flow need not be made for swing compensation. Rather, the determination may be implicitly implemented when considering the following:

FlowFactor=PresDropAcrossTurbine*ImpedOfDeliveryCir/ImpedanceOfTurbine

By applying this FlowFactor to the equation for the adjusted measure of pressure, a further expression may be obtained for the adjustment in measured pressure as follows:

MeasuredPressure$_{Adjusted}$=$P_M$−K*PressureDropAcrossTurbine where

K is a ratio of two impedances such as ImpedOfDeliveryCircuit divided by the ImpedanceOfTurbine.

Such an equation may then be implemented for swing compensation control in a pressure treatment delivery device of the present technology by controlling the respiratory treatment apparatus to generate pressure so that the adjusted measure of pressure meets a target or desired pressure setting.

In the foregoing description and in the accompanying drawings, specific terminology, equations and drawing symbols are set forth to provide a thorough understanding of the present technology. In some instances, the terminology and symbols may imply specific details that are not required to practice the technology. Moreover, although the technology herein has been described with reference to particular embodiments, it is to be understood that these embodiments are merely illustrative of the principles and applications of the technology. It is therefore to be understood that numerous modifications may be made to the illustrative embodiments and that other arrangements may be devised without departing from the spirit and scope of the technology.

For example, the flow estimate technology may be implemented in a system utilized for detecting patient flow limitation or making other adjustments to the delivered treatment pressure of a pressure treatment device. Moreover, the flow estimate may be utilized in systems having a flow sensor. In such a system, the flow estimate technology described herein may serve as back up flow determination in the event of failure of a flow sensor that is used for flow based determinations. Alternatively, the estimate of flow data may be combined with data from a flow sensor to generate combined flow data to insulate the system from more transient errors in either the flow signal from the flow sensor or the derived estimate of flow described herein.

The invention claimed is:

1. A method for determining a flow in a respiratory flow generating apparatus comprising:

determining a measure of pressure produced by a respiratory flow generating apparatus;

determining a measure of a frequency of the respiratory flow generating apparatus;

deriving, with a processor, an estimate of patient respiratory flow as a function of the measure of pressure and the measure of frequency;

triggering, with the processor, an increase in pressure for inspiration by the respiratory flow generating apparatus by comparing the derived estimate of respiratory flow to a first threshold, the first threshold comprising a function of a peak value of a prior respiratory cycle of the derived estimate of respiratory flow; and triggering, with the processor, a decrease in pressure for expiration by the respiratory flow generating apparatus by comparing the derived estimate of respiratory flow to a second threshold, the second threshold being different from the first threshold.

2. The method of claim 1 wherein the measure of frequency is a rotational velocity.

3. The method of claim 2 wherein the deriving comprises determining an expected pressure as a function of the measure of frequency.

4. The method of claim 3 wherein the deriving comprises calculating a difference between the determined expected pressure and the measure of pressure.

5. The method of claim 1 wherein the delivering of the pressure by the respiratory flow generating apparatus comprises triggering an expiratory pressure relief.

6. The method of claim 5 wherein a change in pressure is delivered in synchrony with a patient's respiratory cycle without a measure of the patient's respiratory flow from a flow sensor.

7. The method of claim 1 further comprising adjusting a pressure delivered by the respiratory flow generating apparatus to compensate for a patient induced swing at a patient interface, wherein the adjusting is based on the derived estimate of patient respiratory flow.

8. The method of claim 1, wherein the second threshold is zero.

9. The method of claim 1, wherein the first threshold is a predetermined fraction of the peak value of the prior respiratory cycle of the derived estimate of respiratory flow.

10. The method of claim 9, wherein the predetermined fraction is a quarter.

11. The method of claim 1, further comprising evaluating a predetermined period of time, wherein if the derived estimate of respiratory flow has not exceeded the first threshold within the predetermined period of time, the increase in pressure for inspiration is triggered.

12. The method of claim 11, wherein the predetermined period of time is 15 seconds.

13. An apparatus for generating respiratory flow comprising:

a patient interface to carry a flow of breathable gas to a patient;

a flow generator coupled with the patient interface to generate a flow of the breathable gas through the patient interface;

a pressure transducer to provide a pressure signal indicative of pressure associated with the flow generator;

a tachometer to provide a velocity signal indicative of a speed of the flow generator; and a processor to control the flow generator, the processor coupled with the pressure transducer to process the pressure signal and coupled with the tachometer to process the velocity signal, the processor being configured to control:
  determining a measure of pressure with the pressure signal;
  determining a measure of frequency with the velocity signal; and
  deriving an estimate of patient respiratory flow as a function of the measure of pressure and the measure of frequency;
  triggering an increase in pressure for inspiration by the flow generator by comparing the derived estimate of respiratory flow to a first threshold, the first threshold comprising a function of a peak value of a prior respiratory cycle of the derived estimate of respiratory flow; and
  triggering a decrease in pressure for expiration by the flow generator by comparing the derived estimate of respiratory flow to a second threshold, the second threshold being different from the first threshold.

14. The apparatus of claim 13 wherein the measure of frequency is a rotational velocity.

15. The apparatus of claim 13 wherein the deriving comprises determining an expected pressure as a function of the measure of frequency.

16. The apparatus of claim 15 wherein the deriving comprises calculating a difference between the determined expected pressure and the measure of pressure.

17. The apparatus of claim 13 wherein the control of the generation of pressure with the flow generator comprises triggering an expiratory pressure relief.

18. The apparatus of claim 13 wherein changes in pressure are delivered in synchrony with a patient's respiratory cycle without a measure of the patient's respiratory flow from a flow sensor.

19. The apparatus of claim 13 wherein the processor controls adjusting a pressure delivered by the flow generator to compensate for a patient induced swing at the patient interface, wherein the adjusting is based on the derived estimate of patient respiratory flow.

20. The apparatus of claim 13, wherein the second threshold is zero.

21. The apparatus of claim 13, wherein the first threshold is a predetermined fraction of the peak value of the prior respiratory cycle of the derived estimate of respiratory flow.

22. The apparatus of claim 21, wherein the predetermined fraction is a quarter.

23. The apparatus of claim 13, wherein the processor is further configured to trigger the increase in pressure for inspiration if the derived estimate of respiratory flow has not exceeded the first threshold within a a predetermined period of time.

24. The apparatus of claim 23, wherein the predetermined period of time is 15 seconds.

25. A system for delivering respiratory flow to a patient comprising:
  an interface means to carry a flow of breathable gas;
  a flow means, coupled with the interface means, for generating the breathable gas;
  a pressure sensing means for measuring pressure and for generating a pressure signal representing the measured pressure of the breathable gas;
  a frequency sensing means for measuring a frequency of the flow means and for generating a frequency signal representing the measured frequency;
  a processing means for processing the pressure signal and the frequency signal, the processing means being configured for processing:
    (a) determining a measure of pressure with the pressure signal;
    (b) determining a measure of frequency with the frequency signal;
    (c) deriving an estimate of patient respiratory flow as a function of the measure of pressure and the measure of frequency;
    (d) controlling triggering of an increase in pressure for inspiration with the flow means by comparing the derived estimate of respiratory flow to a first threshold, the first threshold comprising a function of a peak value of a prior respiratory cycle of the derived estimate of patient respiratory flow; and
    (e) controlling triggering of a decrease in pressure for expiration with the flow means by comparing the derived estimate of respiratory flow to a second threshold, the second threshold being different from the first threshold.

26. The system of claim 25 wherein the measure of frequency is a rotational velocity.

27. The system of claim 26 wherein the deriving comprises determining an expected pressure as a function of the measure of frequency.

28. The system of claim 27 wherein the deriving comprises calculating a difference between the determined expected pressure and the measure of pressure.

29. The system of claim 25 wherein the controlling the generation of pressure with the flow means comprises triggering an expiratory pressure relief.

30. The system of claim 29 wherein pressure is delivered in synchrony with a patient's respiratory cycle without a flow sensor.

31. The system of claim 25, wherein the second threshold is zero.

32. The system of claim 25, wherein the first threshold is a predetermined fraction of the peak value of the prior respiratory cycle of the derived estimate of respiratory flow.

33. The system of claim 32, wherein the predetermined fraction is a quarter.

34. The system of claim 25, wherein the processing means is further configured to control triggering of the increase in pressure for inspiration if the derived estimate of respiratory flow has not exceeded the first threshold within a predetermined period of time.

35. The system of claim 34, wherein the predetermined period of time is 15 seconds.

36. A non-transitory information-bearing medium having processor-readable information thereon, the processor-readable information to control an apparatus for providing pressure treatment therapy, the processor-readable information comprising:
  determining a measure of pressure produced by a flow generator;
  determining a measure of frequency of the flow generator; and
  deriving an estimate of patient respiratory flow as a function of the measure of pressure and the measure of frequency;
  triggering an increase in pressure for inspiration by the flow generator by comparing the derived estimate of respiratory flow to a first threshold, the first threshold comprising a function of a peak value of a prior respiratory cycle of the derived estimate of respiratory flow; and triggering a decrease in pressure for expiration by the flow generator by comparing the derived estimate of respiratory flow to a second threshold, the second threshold being different from the first threshold.

37. The information-bearing medium of claim 36 wherein the measure of frequency is a rotational velocity.

38. The information-bearing medium of claim 36 wherein the deriving comprises determining an expected pressure as a function of the measure of frequency.

39. The information-bearing medium of claim 38 wherein the deriving comprises calculating a difference between the determined expected pressure and the measure of pressure.

40. The information-bearing medium of claim 36 wherein the delivering the pressure by the flow generator comprises triggering an expiratory pressure relief.

41. The information-bearing medium of claim 36 wherein a change in pressure is generated in synchrony with a patient's respiratory cycle without a measure of the patient's respiratory flow from a flow sensor.

42. The information-bearing medium of claim 36, wherein the second threshold is zero.

43. The information-bearing medium of claim 36, wherein the first threshold is a predetermined fraction of the peak value of the prior respiratory cycle of the derived estimate of respiratory flow.

44. The information-bearing medium of claim 43, wherein the predetermined fraction is a quarter.

45. The information-bearing medium of claim 36, wherein the processor-readable information further comprises triggering the increase in pressure for inspiration if the derived estimate of respiratory flow has not exceeded the first threshold within a predetermined period of time.

46. The information-bearing medium of claim 45, wherein the predetermined period of time is 15 seconds.

* * * * *